(12) United States Patent
Broadley et al.

(10) Patent No.: US 9,107,011 B2
(45) Date of Patent: Aug. 11, 2015

(54) HEADSET WITH FIT DETECTION SYSTEM

(71) Applicant: Sonetics Holdings, Inc., Vancouver, WA (US)

(72) Inventors: Simon Broadley, West Linn, OR (US); Brian VanderPloeg, Lake Oswego, OR (US)

(73) Assignee: Sonetics Holdings, Inc., Vancouver, WA (US)

(*) Notice: Subject to any disclaimer, the term of this patent is extended or adjusted under 35 U.S.C. 154(b) by 0 days.

(21) Appl. No.: 14/320,926

(22) Filed: Jul. 1, 2014

(65) Prior Publication Data
US 2015/0010158 A1    Jan. 8, 2015

Related U.S. Application Data

(60) Provisional application No. 61/842,830, filed on Jul. 3, 2013.

(51) Int. Cl.
| | |
|---|---|
| *H04R 29/00* | (2006.01) |
| *H04R 1/10* | (2006.01) |
| *H04R 1/08* | (2006.01) |
| H04R 5/033 | (2006.01) |
| H04R 5/04 | (2006.01) |

(52) U.S. Cl.
CPC .............. *H04R 29/00* (2013.01); *H04R 1/08* (2013.01); *H04R 1/1083* (2013.01); *H04R 5/033* (2013.01); *H04R 5/04* (2013.01)

(58) Field of Classification Search
CPC ............ H04R 29/00; H04R 1/08; H04R 1/10; H04R 1/1008; H04R 1/1083; H04R 1/1091; H04R 2420/03; H04R 2420/05; H04R 2420/07; H04R 5/033; H04R 5/04; H04R 27/00; H04R 29/001; H04R 29/004

USPC .............. 381/58, 57, 72, 73.1, 74; 455/575.2; 73/645, 646; 379/430

See application file for complete search history.

(56) References Cited

U.S. PATENT DOCUMENTS

| | | | |
|---|---|---|---|
| 4,625,083 A | 11/1986 | Poikela | |
| 5,852,667 A * | 12/1998 | Pan et al. | ..................... 381/71.1 |
| 6,826,515 B2 | 11/2004 | Bernardi et al. | |
| 7,466,838 B1 * | 12/2008 | Moseley | ........................ 381/370 |
| 7,978,861 B2 | 7/2011 | Michael | |
| 8,391,503 B2 | 3/2013 | Batley et al. | |
| 2002/0076057 A1 * | 6/2002 | Voix | .............................. 381/60 |

(Continued)

*Primary Examiner* — Xu Mei
(74) *Attorney, Agent, or Firm* — Keith L. Jenkins, Registered Patent Attorney, LLC; Keith L. Jenkins

(57) ABSTRACT

Headphones with acoustically resistant ear cups, an external noise sensor mounted thereto that monitors ambient noise, and internal sensors to monitor noise within each ear cup are disclosed. A processing system monitors the external and interior sound detected by the sensors and compares the level inside the ear cups with the detected level of ambient noise. It activates a transducer such as a vibrator, buzzer, or light as needed to indicate when the level within the ear cups has exceeded the predetermined criteria thereby indicating improper fit of the headphones. Alternative embodiments include wirelessly communicating the collected data to an auxiliary computer for remote data collection, storage and monitoring. The headphones may also provide a sound dosimeter; bandpass filtering; automatic noise reduction with feed forward and/or feed back; wireless voice and data communication; and a voice activated switch, all using elements of the headphone fit detection circuitry.

20 Claims, 12 Drawing Sheets

(56) References Cited

U.S. PATENT DOCUMENTS

| | | | |
|---|---|---|---|
| 2003/0095670 A1* | 5/2003 | Wurtz | 381/71.6 |
| 2007/0154049 A1* | 7/2007 | Levitsky et al. | 381/371 |
| 2008/0165981 A1* | 7/2008 | Wurtz | 381/71.6 |
| 2009/0022353 A1* | 1/2009 | Goldstein et al. | 381/380 |
| 2009/0034748 A1* | 2/2009 | Sibbald | 381/71.6 |
| 2010/0074451 A1* | 3/2010 | Usher et al. | 381/58 |
| 2014/0003613 A1* | 1/2014 | Sibbald | 381/71.6 |
| 2014/0010378 A1* | 1/2014 | Voix et al. | 381/57 |
| 2014/0146989 A1* | 5/2014 | Goldstein | 381/380 |

* cited by examiner

HEADSET WITH FIT DETECTION SYSTEM

RELATED APPLICATIONS

This application claims priority to U.S. provisional patent application Ser. No. 61/842,830 filed on Jul. 3, 2013 the disclosure of which is hereby incorporated by reference.

TECHNICAL FIELD

This invention relates to providing a headset that detects when it is being improperly worn by a user and makes an alarm or notification that the headset is not properly worn. The invention also relates to audio headsets that are wireless.

BACKGROUND

Headphones and headsets are used for hearing protection and for communication in a variety of industrial settings. As used and defined herein, the terms "headset" and headphone" are used interchangeably to refer to devices that engage a user's ears to provide sound, noise protection, or both for the user.

The human audio frequency band is generally 20 Hz to 20 kHz, however, some frequency sub-bands, such as 63 Hz to 8 kHz within the human audio frequency band are of special interest for hearing protection. Headsets typically include two ear cups edged with a soft material to make a sound-resistant seal between the ear cups and the user's head and a head band adjustably connecting the two ear cups. Headsets that provide both hearing protection and wireless communications are of particular interest, as the communications speaker with external noise penetrating the ear cup can contribute to the total noise dose. OSHA sets standards for hearing protection in high-noise environments, such as factories and flight lines. Headsets are often worn improperly due to user preferences that are at variance with best safety practices. Eyeglass stems, jewelry, or other accessories worn by the user may also impact the effectiveness of the sound-resistant seal. Knowing this, OSHA derates hearing protection devices from the technical capability of the actual hearing protection headset to a lower rating to take improper fit into consideration. Consequently, hearing protection devices must be over-designed and over-constructed to still qualify for use after the derating. Overcompensating for improperly used hearing protection increases costs of providing hearing protection.

U.S. Pat. No. 8,391,503 B2 issued 2013 Mar. 5 to Bayley et al., discloses a system for measuring noise exposure associated with use of a wireless headset. Bayley does not address fit detection. U.S. Pat. No. 6,826,515 B2 issued 2004 Nov. 30 to Bernardi et al. discloses an apparatus for monitoring and controlling exposure to noise related to a headset by changing the gain on the voice input to ensure that total noise does not exceed a threshold. Bernardi does not address fit detection. U.S. Pat. No. 4,625,083 issued 1986 Nov. 25 to Poikela discloses dual microphones, one for speech and one for ambient external noise, for independently processing noise and voice. Poikela does not address fit detection. U.S. Pat. No. 7,978,861 B2 issued 2011 Jul. 12 to Michael discloses A method for continuously monitoring noise exposure level of a person via measuring sound level within an ear canal of the person. Michael does not address fit detection.

Therefore, a need exists for a hearing protection headset that can detect when it is being improperly worn and report this detection at least to the user.

Objects and Features of the Invention

A primary object and feature of an embodiment of the present invention is to overcome the above-mentioned problems and fulfill the above-mentioned needs.

Another object and feature of an embodiment of the present invention is to provide a system that provides a notification when a hearing protection headset does not fit or is not being properly worn.

It is a further object and feature of an embodiment of the present invention to provide a system that provides the notification to the wearer and/or to a remote display.

It is a further object and feature of an embodiment of the present invention to provide a system that provides the notification by visual, audible, and/or tactile means.

It is a further object and feature of an embodiment of the present invention to provide a system that measures the sound dose experienced by the user over time.

It is a further object and feature of an embodiment of the present invention to provide a system that measures the sound dose experienced by the user over time and to report the dose to the user and/or store the data in a database.

It is a further object and feature of an embodiment of the present invention to provide a system that measures the sound dose experienced by the user over time and actively limits any incoming audio transmissions to ensure a predetermined sound dose is not exceeded.

It is a further object and feature of an embodiment of the present invention to provide a system that includes at least one of active noise reduction, a voice activated switch, wireless voice communication, and a sound dosimeter.

It is a further object and feature of an embodiment of the present invention to provide a system that prevents wireless voice communication from increasing the sound power level to the user's ear above a predetermined safe level.

It is a further object and feature of an embodiment of the present invention to provide a system that provides a notification when a hearing protection headset does not fit or is not being properly worn and also provides one or more of: automatic noise reduction with feed forward, feedback, or combined feed forward and feedback control, a voice-activated switch, wireless audio communication, bandpass filtering of problematic frequencies, and a sound dosimeter.

It is an additional primary object and feature of an embodiment of the present invention to provide such a system that is efficient, inexpensive and handy. Other objects and features of this invention will become apparent with reference to the following descriptions.

SUMMARY OF THE INVENTION

Thus, despite the known improvements to headphones, there remains a need for headphones that monitor, determine, and alert, in real time, when they are not being worn properly and thereby compromising their acoustic benefits. In addition, to other benefits that will become apparent herein, the present invention fulfills these needs.

Thus, despite the known improvements to headphones, there remains a need for headphones that monitor, determine, and alert, in real time, when they are not being worn properly and thereby compromising their acoustic benefits. In addition, to other benefits that will become apparent herein, the present invention fulfills these needs.

In one disclosed embodiment, the headphones have acoustically isolating ear cups that encircle the wearer's ears. An external sound sensor is secured to each of the headphones to monitor ambient sound and an internal sound sensor is mounted inside each of the ear cups to monitor sound within each ear cup. A processing subsystem, which may be a computer system, monitors the external and interior sound detected by the sensors and compares the sound level inside each of the ear cups plus a fit allowance with the sound outside each respective ear cup to determine if the external sound level is greater than the sum of the internal sound level and the fit allowance. The processing subsystem activates a transducer such as a vibrator, buzzer, wireless communication, and/or light as needed to indicate when the level within the ear cups has exceeded the predetermined criteria. Accordingly, if the wearer is wearing the headphones improperly such that the wearer's ears are not protected from excess sound, the headphone will alert the wearer of this situation in real time giving the wearer an opportunity to correct the situation before being inadvertently exposed for long periods of time to the excess sound.

Alternative embodiments include wirelessly communicating the collected data to an auxiliary computer for data recorder at a remote monitoring system and to alert other workers of any detected problems.

Additional embodiments of the headset may additionally feature active noise reduction, a voice-activated switch, wireless voice communication, and a sound dosimeter using at least some of the resources common to the system for determining a fitment.

The advantages and features of novelty characterizing aspects of the invention are pointed out with particularity in the appended claims. To gain an improved understanding of the advantages and features of novelty, however, reference may be made to the following descriptive matter and accompanying figures that describe and illustrate configurations and concepts related to the invention.

The headset may additionally feature active noise reduction, a voice-activated switch, wireless voice communication, and a sound dosimeter using at least some of the resources common to the system for determining a fitment.

The invention includes a headset having hearing protection for at least one of its purposes, the headset including: an ear cup having a sound-resistant edge seal; a first microphone mounted on the exterior of the ear cup; a second microphone mounted on the interior of the ear cup; a signal processor, coupled to the first microphone and to the second microphone, for computing external and internal sound pressure levels, respectively, from first and second signals from the first and the second microphones, respectively; and a non-volatile memory coupled to the signal processor for storing a constant representing a fit allowance, where the fit allowance is a number representing the predetermined difference between the internal sound pressure level and the external sound pressure level when the headset is worn properly. The headset, further including a logic coupled to the signal processor and to the non-volatile memory and operable to add the constant to the internal sound pressure level to obtain an adjusted internal sound pressure level and compare the adjusted internal sound pressure level to the external sound pressure level to determine if the external sound pressure level is greater than or equal to the adjusted internal sound pressure level; and a notification system coupled to the logic and responsive to the determination to produce a notification if the determination is that the external sound pressure level is not greater than or equal to the adjusted internal sound pressure level. The headset, where the first microphone includes a plurality of first microphones at least one of which has an output signal bandpass-filtered for a predetermined frequency band that is a subset of a human audio frequency band; and the second microphone includes a plurality of second microphones at least one of which has an output signal bandpass-filtered for a predetermined frequency band that is a subset of the human audio frequency band. The headset, where the notification device includes an audio speaker inside the ear cup. The headset, where the signal processor and the logic implement active noise reduction using either the first signal and the audio speaker or the second signal as a feedback signal and the audio speaker. The headset, where the signal processor and the logic implement active noise reduction using the first signal, the second signal, and the audio speaker. The headset, further including a wireless receiver communicatively coupled to the signal processor and coupled to the audio speaker for receiving wireless audio communications in the ear cup. The headset, further including a volatile memory coupled to the signal processor and to the logic. The headset, where the signal processor and the logic implement a sound dosimeter using the second signal and the volatile memory. The headset, where the notification device includes a plurality of notification devices, at least one of which is operable to provide information related to an output of the sound dosimeter in human-readable form. The headset, where the notification system includes: an audio speaker mounted inside the ear cup; a tactile stimulator mounted on the headset; a visual stimulator mounted on the headset; and a wireless transmitter mounted on the headset, a wireless receiver, and a display device operable to display information related to the notification in human-readable form. The headset, further including a boom microphone mounted on the headset and capable of being oriented near a user's mouth, an audio speaker mounted inside the ear cup, a wireless transmitter mounted on the headset, and a wireless receiver mounted on the headset, together operable to provide wireless audio communication. The headset, where the signal processor and the logic restrict an output of the audio speaker sound power level to maintain a sound power level inside the ear cup below a predetermined limit. The headset, where the signal processor and the logic implement a voice-activation switch using the first microphone and the boom microphone.

The invention also includes a headset having hearing protection for at least one of its purposes, the headset including: a ear cup having a sound-resistant edge seal; a first microphone mounted on the exterior of the ear cup; a second microphone mounted on the interior of the ear cup; a signal processor, coupled to the first microphone and to the second microphone, for computing external and internal sound pressure levels, respectively, from first and second signals from the first microphone and the second microphone, respectively; a non-volatile memory coupled to the signal processor for storing a constant representing a fit allowance, where the fit allowance is a number representing the predetermined difference between the internal sound pressure level and the external sound pressure level when the headset is worn properly; a logic coupled to the signal processor and to the non-volatile memory and operable to add the constant to the internal sound pressure level to obtain an adjusted internal sound pressure level and to compare the adjusted internal sound pressure level to the external sound pressure level to determine if the external sound pressure level is greater than or equal to the adjusted internal sound pressure level; a notification system coupled to the logic and responsive to the determination to produce a notification if the determination is that the external sound pressure level is not greater than or equal to the adjusted internal sound pressure level; and a volatile memory coupled to the signal processor and to the logic. The headset, where the first microphone includes a plurality of first microphones at least one of which has an output signal bandpass-filtered for a predetermined frequency band that is a subset of a human audio frequency band; and the second microphone includes a plurality of second microphones at least one of which has an output signal bandpass-filtered for a predetermined frequency band that is a subset of a human audio frequency band. The headset, where the notification system includes an audio speaker mounted inside the ear cup; an audio speaker mounted on the headset; a tactile stimulator mounted on the headset; a visual stimulator mounted on the headset; and/or a wireless transmitter mounted on the headset with a wireless receiver and a display device operable to display information related to the notification in human-readable form. The headset, where the signal processor and the logic implement active noise reduction using the first signal as a feed forward signal and the audio speaker; active noise reduction using the first signal as a feed forward signal, a second signal as a feedback signal, and the audio speaker; active noise reduction using the second signal as a feedback signal and the audio speaker; a voice-activation switch using the first microphone and a boom microphone coupled to the headset; and/or a sound dosimeter using the second signal and the volatile memory, where the notification system includes a subsystem operable to provide information related to an output of the sound dosimeter in machine-readable and/or human-readable form.

Another embodiment of the invention includes a headset having hearing protection for a of its purposes, the headset including: a ear cup having a sound-resistant edge seal; a first microphone mounted on the exterior of the ear cup; a second microphone mounted on the interior of the ear cup; a signal processor, coupled to the first microphone and to the second microphone, for computing external and internal sound pressure levels, respectively, from first and second signals from the first microphone and the second microphone, respectively; a non-volatile memory coupled to the signal processor for storing a constant representing a fit allowance, where the fit allowance is a number representing the predetermined difference between the internal sound pressure level and the external sound pressure level when the headset is worn properly; a logic coupled to the signal processor and to the non-volatile memory and operable to add the constant to the internal sound pressure level to obtain an adjusted internal sound pressure level; and compare the adjusted internal sound pressure level to the external sound pressure level to determine if the external sound pressure level is greater than or equal to the adjusted internal sound pressure level; a notification system coupled to the logic and responsive to the determination to produce a notification if the determination is that the external sound pressure level is not greater than or equal to the adjusted internal sound pressure level; where the notification system includes an audio speaker mounted inside the ear cup; an audio speaker mounted on the headset; a tactile stimulator mounted on the headset; a visual stimulator mounted on the headset; and/or a wireless transmitter mounted on the headset, a wireless receiver, and a display device operable to display a notification in machine-readable and/or human-readable form; a volatile memory coupled to the signal processor and to the logic. The headset, where: the first microphone includes a plurality of first microphones at least one of which has an output signal bandpass-filtered for a predetermined frequency band that is a subset of a human audio frequency band; the second microphone includes a plurality of second microphones at least one of which has an output signal bandpass-filtered for a predetermined frequency band that is a subset of a human audio frequency band; and where the signal processor and the logic additionally implement active noise reduction using the first signal as a feed forward signal and the audio speaker; active noise reduction using the first signal as a feed forward signal, a second signal as a feedback signal, and the audio speaker; active noise reduction using the second signal as a feedback signal and the audio speaker; a voice-activation switch using the first microphone and a boom microphone coupled to the headset; and/or a sound dosimeter using the second signal and the volatile memory, where the notification system includes a subsystem operable to provide notification of an output of the sound dosimeter in machine-readable and/or human-readable form.

BRIEF DESCRIPTION OF THE DRAWINGS

The present invention will hereinafter be described in conjunction with the following drawing figures, wherein like numerals denote like elements and the hundreds digits denote the drawing number in which the item is first referenced.

DETAILED DESCRIPTION OF THE PRESENT INVENTION

As used and defined herein, "human audio frequency band" means 20 Hz to 20 kHz, and any and all sub-bands therein. As used and defined herein, the terms "headset" and headphone" are used interchangeably to refer to devices that engage a user's ears to provide sound, noise protection, or both for the user.

Figure 1:
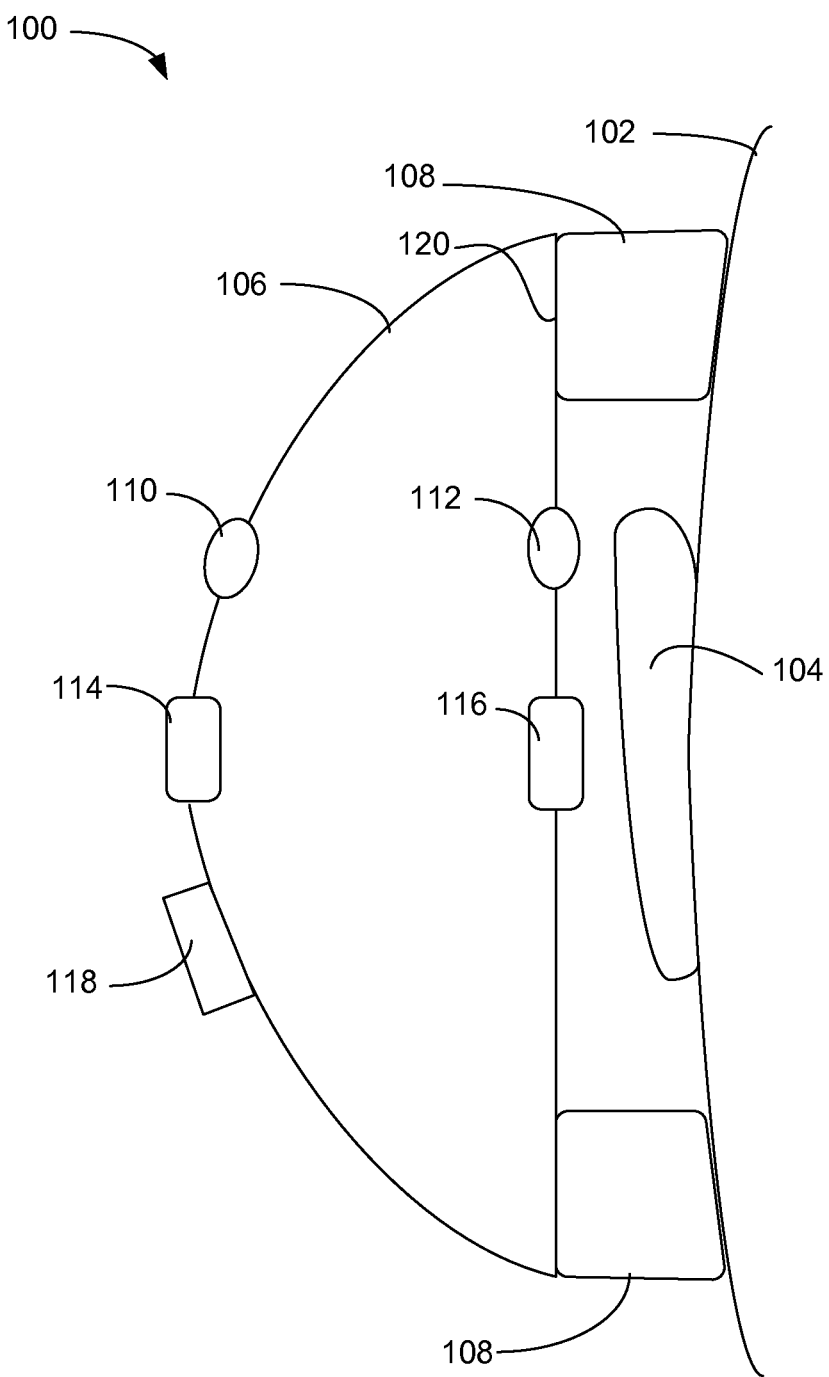
FIG. 1 is a front elevation diagrammatic view illustrating a first exemplary embodiment of the headset with fit detection system, according to a preferred embodiment of the present invention.

FIG. 1 is a front elevation diagrammatic view illustrating a first exemplary embodiment of the headset with fit detection system 100, according to a preferred embodiment of the present invention. The headset includes one or two ear cups 106 and a headband, as known in the art, for securing the ear cup to the head 102. Ear cup 106 covers ear 104 of head 102 of a user in need of hearing protection. The circumferential edge 120 of ear cup 106 supports sound resistant cushion seal 108 that engages the user's head 102. System 100 includes an external sound detection sensor such as an external microphone 110 mounted on the exterior of the ear cup 106 and an internal sound detection sensor such as an internal microphone 112 mounted on the inside of the ear cup 106. Both external microphone 110 and internal microphone 112 are communicatively coupled to a processing subsystem 118, which compares the interior sound power level (SPL) and the exterior SPL, based on the outputs of each external microphone 110 and respective internal microphone 112 to determine if the headset 100 is providing the intended hearing protection. In various embodiments, processing subsystem 118 may be mounted on the outside of ear cup 106, as shown, the inside of the ear cup 106, mounted on the headband, or distributed between any combination of the inside and outside of ear cups 106 and the headband. In various embodiments, processing subsystem 118 may include, for non-limiting examples, a digital signal processor (DSP) 302, a logic 304, and a non-volatile memory 308 (as illustrated); a computer system; or an analog signal processor, a non-volatile memory 308, and a logic 304.

Notification device 114 and notification device 116 activate responsive to a determination by processing subsystem 118 that the headset is not providing the intended protection. Notification device 116 may be an audio speaker, an audio alarm, a visual display, or a tactile stimulator. Notification device 114 may be an audio speaker, an audio alarm, a tactile stimulator, a visual stimulator, a visual display, a wired transmitter, or a wireless transmitter.

Figure 2:
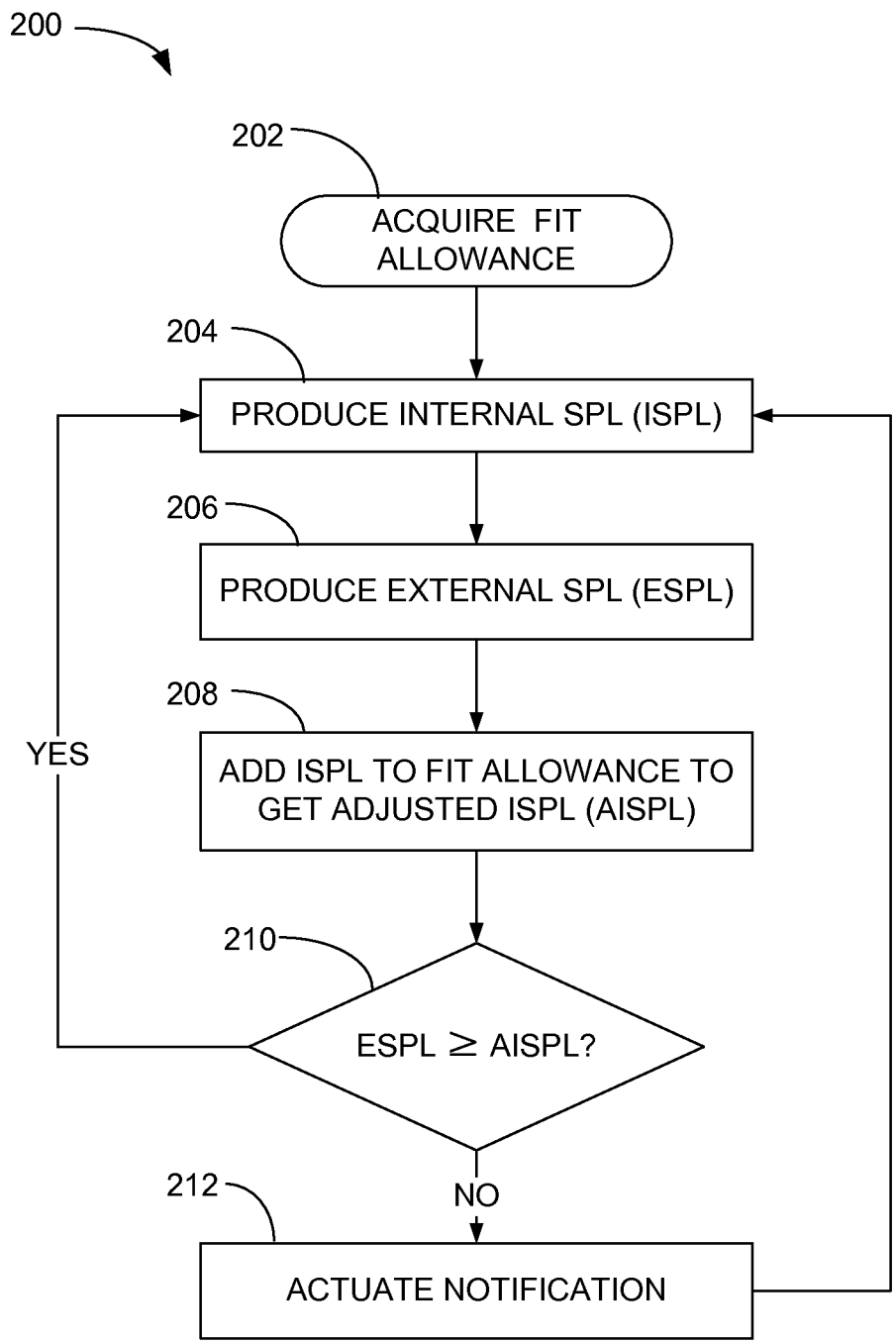
FIG. 2 is a flow chart illustrating a first exemplary embodiment of a process of the headset with fit detection system of FIG. 1, according to a preferred embodiment of the present invention.

FIG. 2 is a flow chart illustrating a first exemplary embodiment of a process 200 of the headset with fit detection system 100 of FIG. 1, according to a preferred embodiment of the present invention. In step 202, the system 100 acquires a fit allowance, preferably from non-volatile memory 308 (see FIG. 3) in processing subsystem 118, where the fit allowance was stored during manufacture or user programming. The fit allowance is the number of decibels of difference that there should be between the external SPL and the internal SPL, based on the processed outputs of external microphone 110 and internal microphone 112, if the headset is performing as desired.

In step 204, processing subsystem 118 produces the internal SPL from the output of internal microphone 112. Various methods of computing SPL are known in the art. The method for computing the SPL in the United States, for example, is established by the Occupational Safety and Health Administration (OSHA). A digital signal processor (DSP) 302 (see FIG. 3) within processing subsystem 118 is preferably used for computing SPLs from microphone 110 and 112 outputs. In step 206, processing subsystem 118 produces the external SPL from the output of external microphone 110. The DSP 302 is merely exemplary and, in another embodiment, the function of the DSP 302 may be performed by analog circuitry.

In step 208, the fit allowance and the internal SPL are added (both quantities being in decibels, for example) to produce an adjusted internal SPL which is then compared, in step 210, to the external SPL. If the external SPL is greater than or equal to the adjusted internal SPL, then the headset 100 is performing as desired and the process continues at step 204. If the external SPL is not greater than or equal to the adjusted internal SPL, then the headset 100 is not performing as desired and a notification is made in step 212.

In an additional embodiment, the fit allowance can be subtracted from the external SPL and the same comparison 210 made.

Figure 3:
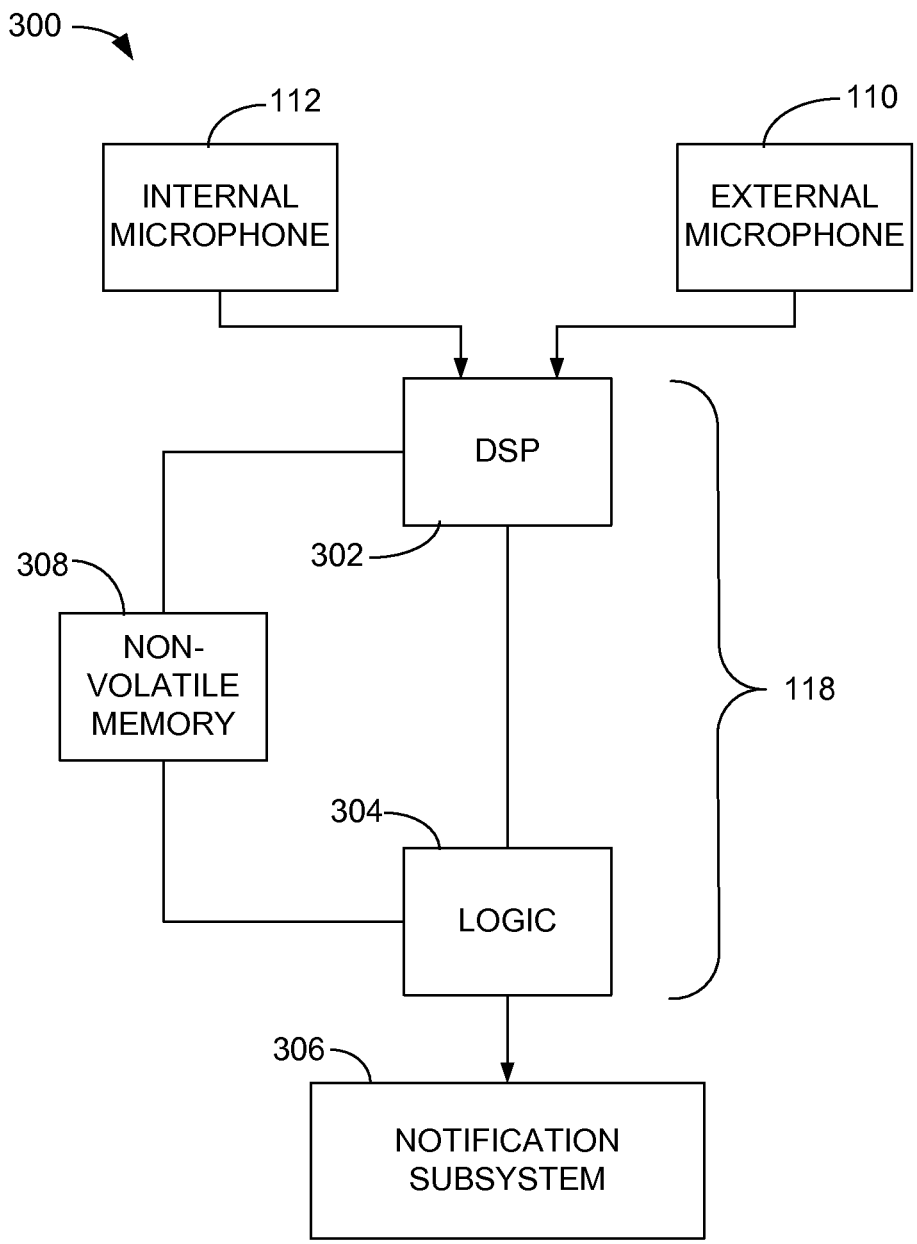
FIG. 3 is a diagrammatic view illustrating a first exemplary embodiment of an electronic subsystem of the headset with fit detection system of FIG. 1, according to a preferred embodiment of the present invention.

FIG. 3 is a diagrammatic view illustrating a first exemplary embodiment of an electronic subsystem 300 of the headset with fit detection system 100 of FIG. 1, according to a preferred embodiment of the present invention. Electronic processing subsystem 118 includes DSP 302, logic 304, and non-volatile memory 308. Logic 304 may be, for non-limiting example, a microprocessor. In various other embodiments, logic 302 may have a locally distributed architecture. DSP 302 receives inputs from external microphone 110 and internal microphone 112 and produces (steps 204 and 206) an SPL for each microphone 110 and 112. Addition 208 and comparison 210 may be done in logic 304. In some embodiments, addition 208 and comparison 210 may be done in DSP 302. Notification subsystem 306 receives a determination from the electronic processing system 118 that the headset 100 is not performing properly and provides notification to the user and, preferably, to a monitor, such as a remote monitor.

Figure 4:
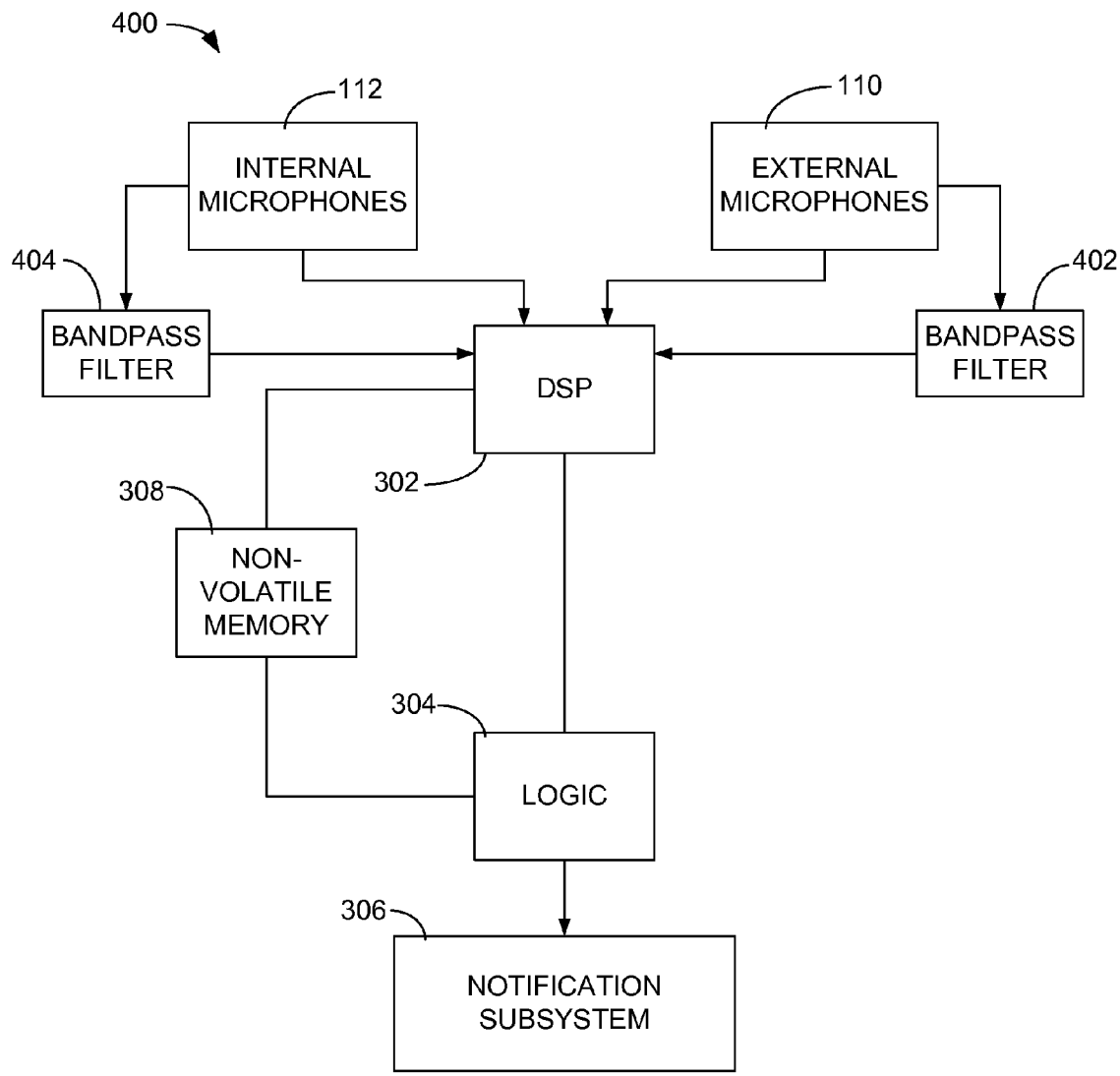
FIG. 4 is a diagrammatic view illustrating a second exemplary embodiment of an electronic subsystem of the headset with fit detection system of FIG. 1, according to a preferred embodiment of the present invention.

FIG. 4 is a diagrammatic view illustrating a second exemplary embodiment of an electronic subsystem 400 of the headset with fit detection system 100 of FIG. 1, according to a preferred embodiment of the present invention. To accommodate various noise standards, bandpass filter 404 may be adjusted for different filters as required by each standard. The filter may be A-Weighted, B-Weighted, C-Weighted, or any other filter as required by a hearing protection standard. In another embodiment, the bandpass filter 404 may be physically collocated with internal microphone 112. In still yet another embodiment, filter 404 may be physically collocated with DSP 302. In yet another embodiment, bandpass filter 404 may be a function within DSP 302. Bandpass filter 402 works in the same manner as bandpass filter 404, but acts on the eternal sound signal from one external microphone 110. The remainder of electronic subsystem 400 operates as the embodiment described with respect to FIG. 3.

Figure 5:
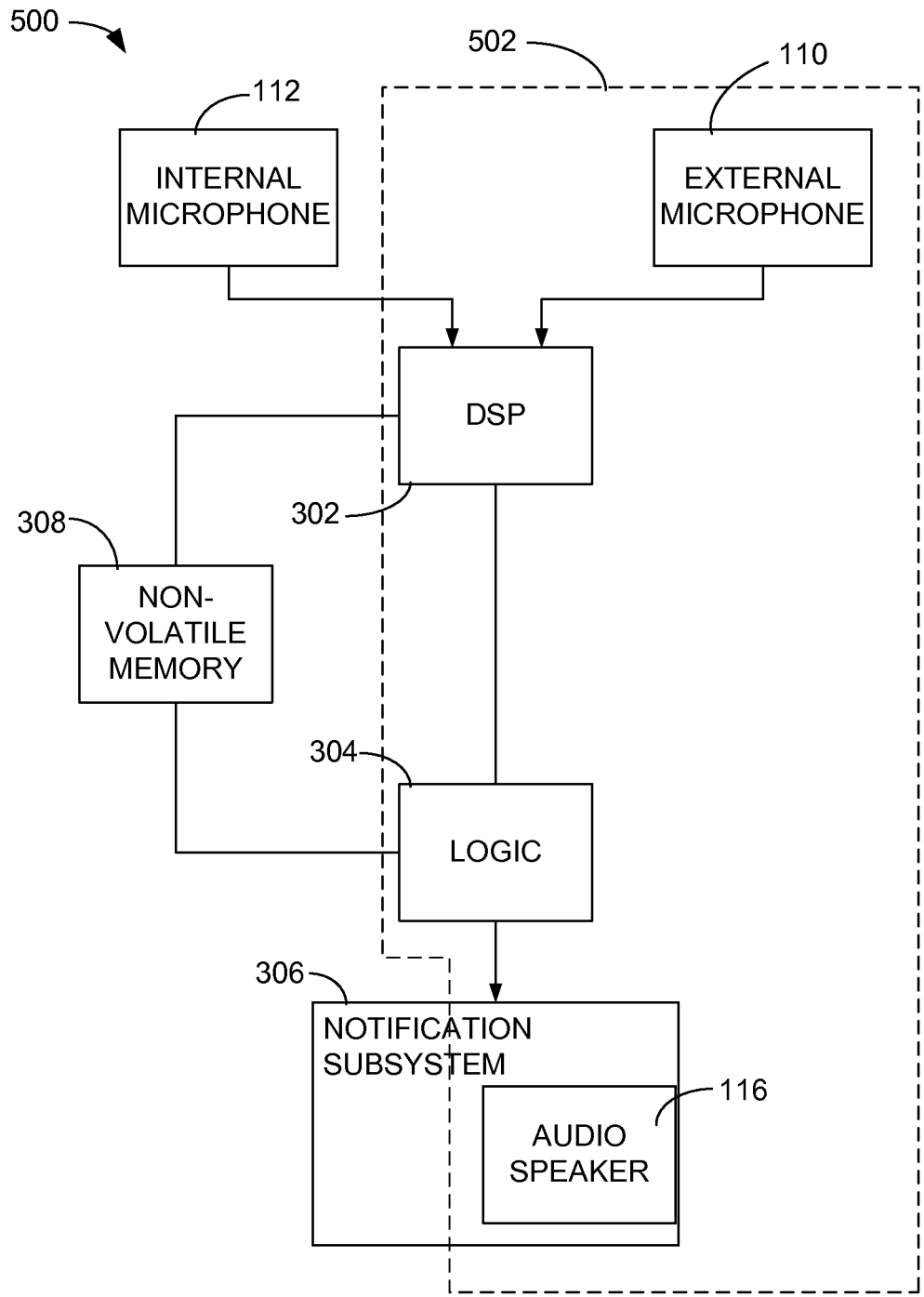
FIG. 5 is a diagrammatic view illustrating a third exemplary embodiment of an electronic subsystem of the headset with fit detection system of FIG. 1 featuring ANR with a feed forward signal, according to a preferred embodiment of the present invention.

FIG. 5 is a diagrammatic view illustrating a third exemplary embodiment of an electronic subsystem 500 of the headset with fit detection system 100 of FIG. 1 featuring automatic noise reduction (ANR) 502 with a feed forward signal, according to a preferred embodiment of the present invention. Notification subsystem 306 includes internal audio speaker 116. The DSP 302 uses the output of external microphone 110 as, among other things, a feed forward noise signal to generate an inverted signal version of the noise signal to drive audio speaker 116 to assist in cancelling the noise within ear cup 106. Logic 304 contains the ANR control system logic to use the feed forward signal from external microphone 110.

Figure 6:
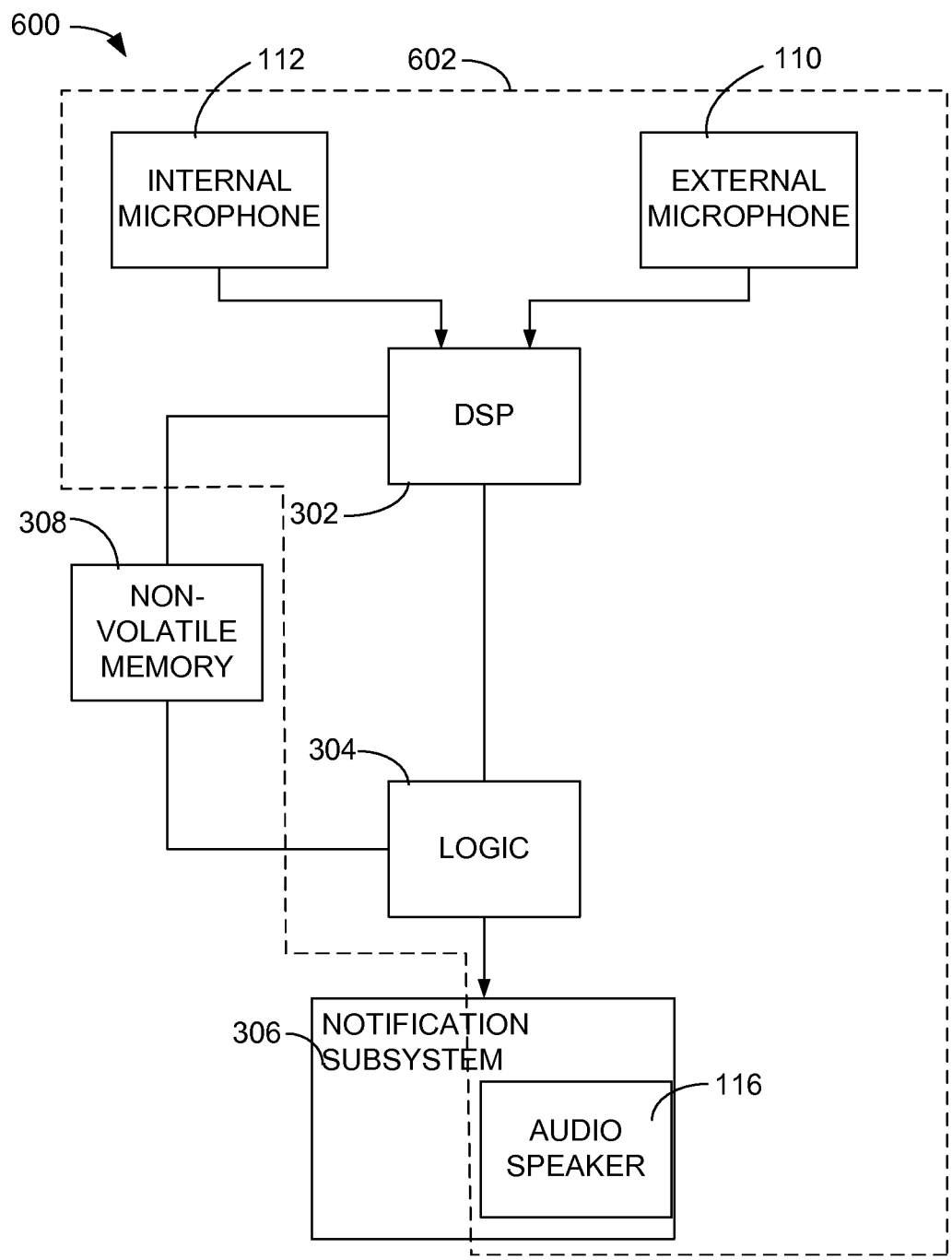
FIG. 6 is a diagrammatic view illustrating a fourth exemplary embodiment of an electronic subsystem of the headset with fit detection system of FIG. 1 featuring ANR with a feed forward and a feedback signal, according to a preferred embodiment of the present invention.

FIG. 6 is a diagrammatic view illustrating a fourth exemplary embodiment of an electronic subsystem of the headset with fit detection system 100 of FIG. 1 featuring ANR 602 with a feed forward and a feedback signal, according to a preferred embodiment of the present invention. Similar to the ANR 502 of FIG. 5, the ANR 602 of FIG. 6 adds the internal microphone 112 as a source of a feedback signal for the ANR 602 control in logic 304. In a particular embodiment, an ANR with no feed forward signal from external microphone 110 may be used with only feedback from internal microphone 112.

Figure 7:
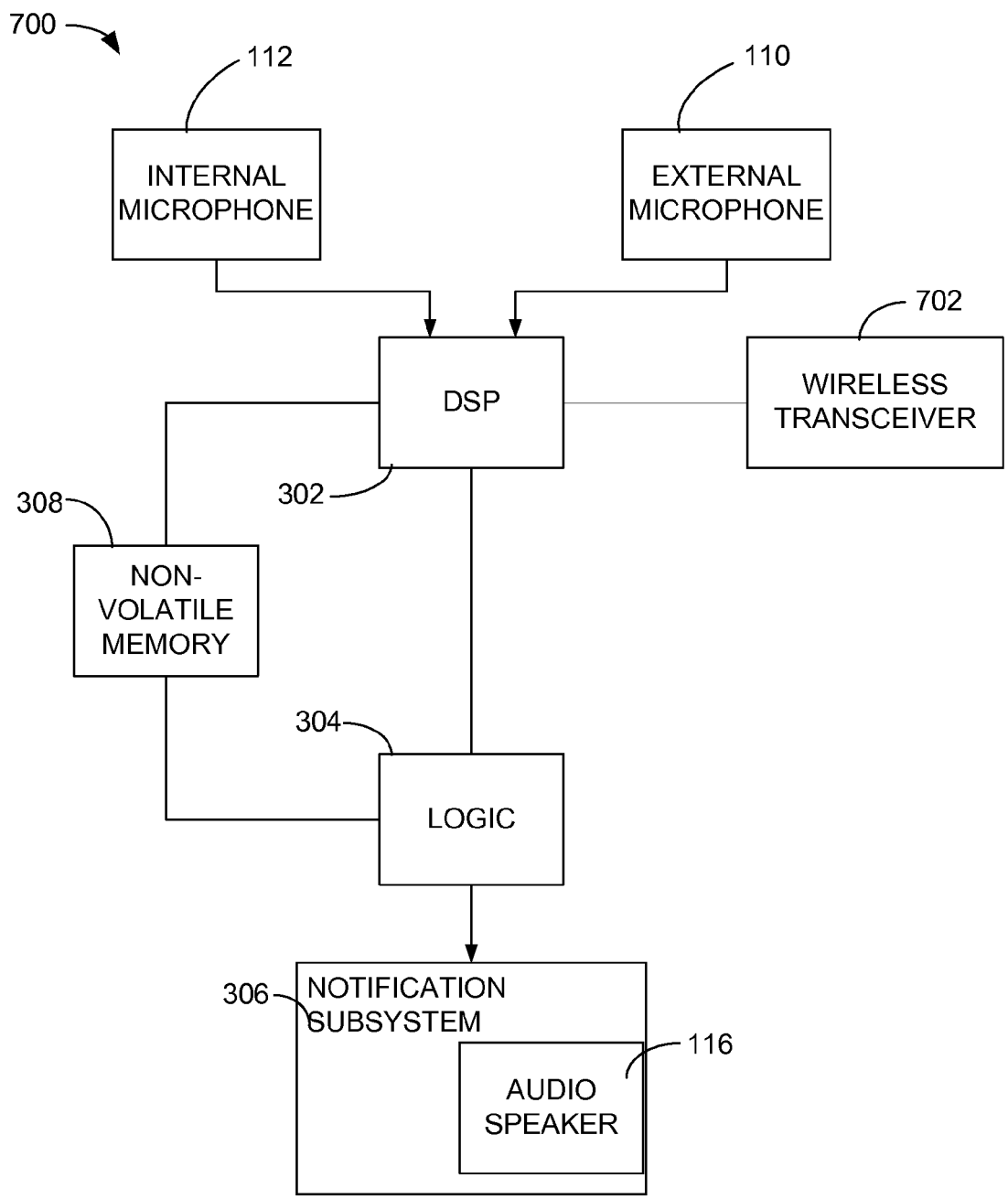
FIG. 7 is a diagrammatic view illustrating a fifth exemplary embodiment of an electronic subsystem of the headset with fit detection system of FIG. 1 having a wireless input, according to a preferred embodiment of the present invention.

FIG. 7 is a diagrammatic view illustrating a fifth exemplary embodiment of an electronic subsystem 700 of the headset with fit detection system 100 of FIG. 1 having a wireless transceiver 702, according to a preferred embodiment of the present invention. The wireless transceiver 702 adds wireless communication to the headset. The wireless communication may use any available protocol. For non-limiting example, DECT, Bluetooth, or CDMA protocols may be used.

Figure 8:
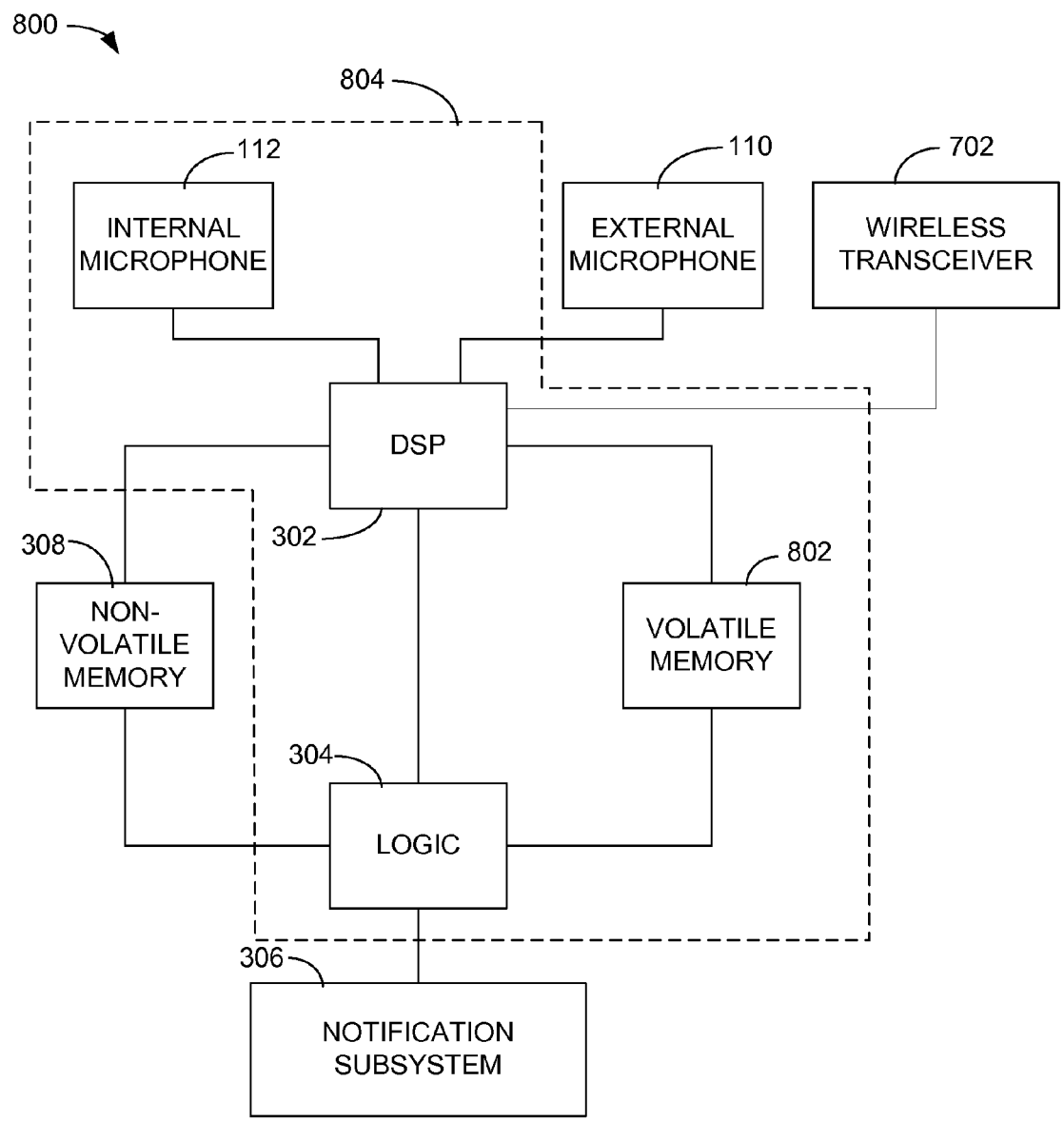
FIG. 8 is a diagrammatic view illustrating a sixth exemplary embodiment of an electronic subsystem of the headset with fit detection system of FIG. 1 with volatile memory and usable as a sound dosimeter, according to a preferred embodiment of the present invention.

FIG. 8 is a diagrammatic view illustrating a sixth exemplary embodiment of an electronic subsystem 800 of the headset with fit detection system 100 of FIG. 1 with volatile memory 802 and implements a sound dosimeter 804, according to a preferred embodiment of the present invention. DSP 302 and logic 304 may share the task of calculating the cumulative time weighted average dose and monitoring the peak SPLs. The dose and peak data are stored in volatile memory 802. Data may be transmitted out through a wireless transceiver 702 to be stored in an external database or to be monitored in real time. In a particular embodiment the output of dosimeter 804 is preferably provided in human readable form. In various other embodiments, other output forms, such as, without limitation, machine-readable or visual alarm.

Figure 9:
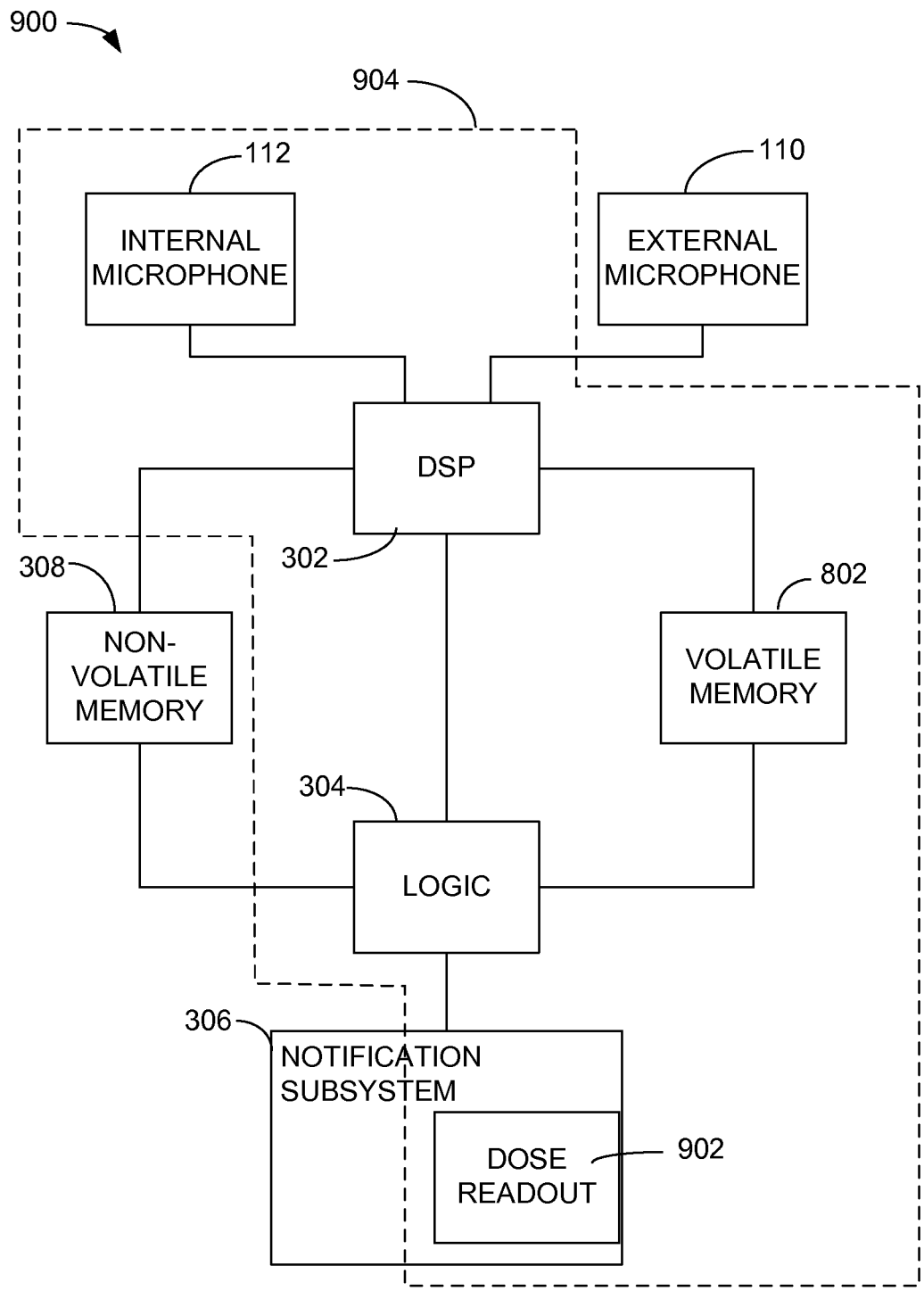
FIG. 9 is a diagrammatic view illustrating a seventh exemplary embodiment of an electronic subsystem of the headset with fit detection system of FIG. 1 with volatile memory and usable as a sound dosimeter with a readout, according to a preferred embodiment of the present invention.

FIG. 9 is a diagrammatic view illustrating a seventh exemplary embodiment of an electronic subsystem 900 of the headset with fit detection system 100 of FIG. 1 with volatile memory 802 and usable as a sound dosimeter 904 with a readout 902, according to a preferred embodiment of the present invention. Dose readout 902, a portion of notification subsystem 306, provides the output of sound dosimeter 904 to the user. At the end of a usage period, the user can observe the dose readout 902 to determine the user's exposure over the usage period. Dose readout 902 may be as simple as an indicator light that turns on to show that permissible dosage was exceeded or as convenient as a small digital touch screen that provides detailed numerical dose data.

Figure 10:
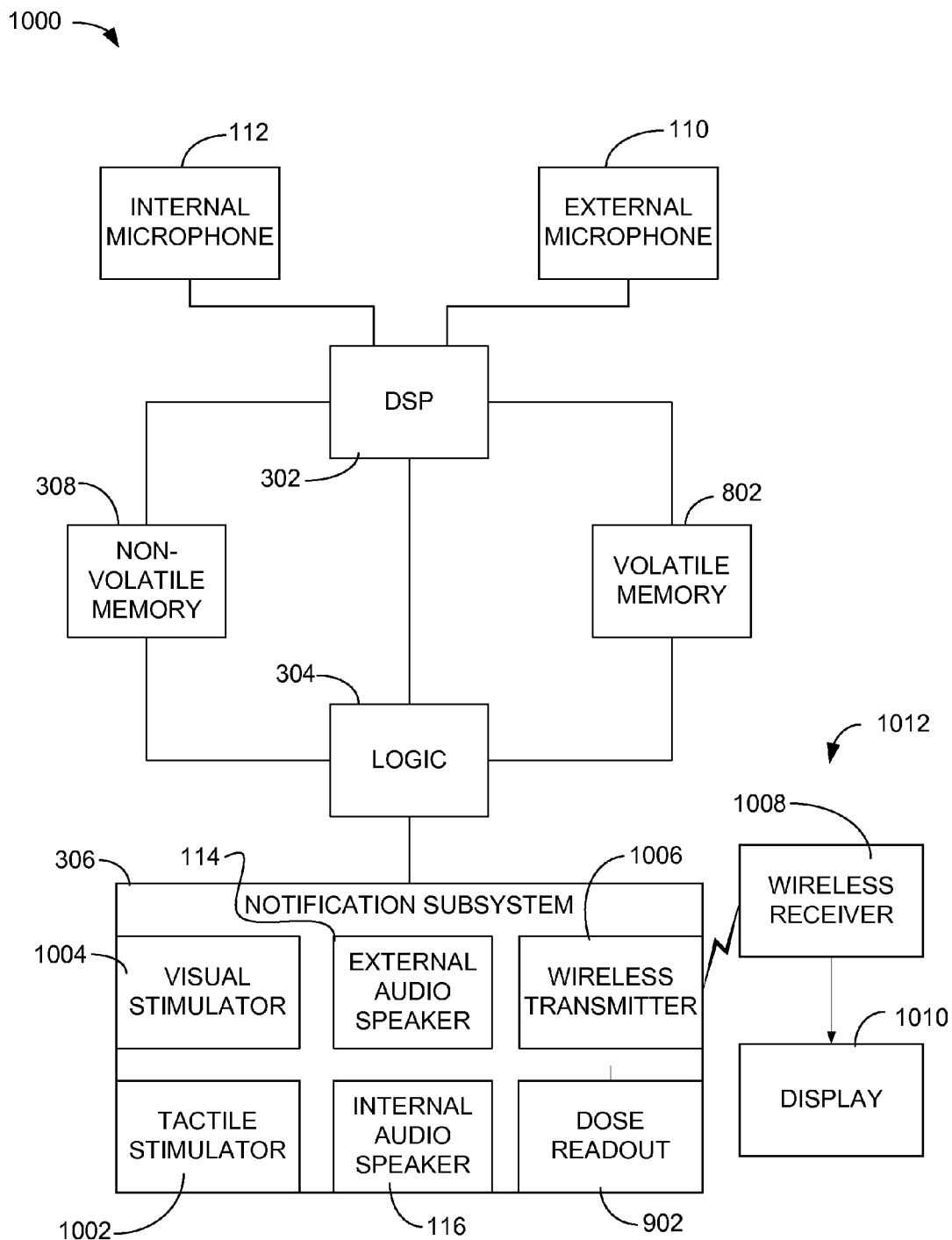
FIG. 10 is a diagrammatic view illustrating a eighth exemplary embodiment of an electronic subsystem of the headset with fit detection system of FIG. 1 with volatile memory and having a wireless readout subsystem, according to a preferred embodiment of the present invention.

FIG. 10 is a diagrammatic view illustrating a eighth exemplary embodiment of an electronic subsystem 1000 of the headset with fit detection system 100 of FIG. 1 with volatile memory 802 and having a wireless readout subsystem 1012, according to a preferred embodiment of the present invention. Notification subsystem 306 may include a wireless readout subsystem 1012 that includes a wireless transmitter 1006 coupled to the headset 100 and a remote wireless receiver 1008 coupled to a display 1010 for presenting the received data. Data from volatile memory 802 may be provided to a remote safety monitor using wireless readout subsystem 1012. The data may include, without limitation, dose, peak SPLs, and fitment notifications.

Notification subsystem 306 may include a tactile stimulator 1002, mounted on the headset, that vibrates or touches the user to indicate that the headset is not being properly worn. Notification subsystem 306 may also include a visual stimulator 1004, mounted on the headset, that may be, for non-limiting example, a flashing light 1004 intended for a safety monitor to see or a flashing light 1004 within view of the user.

Figure 11:
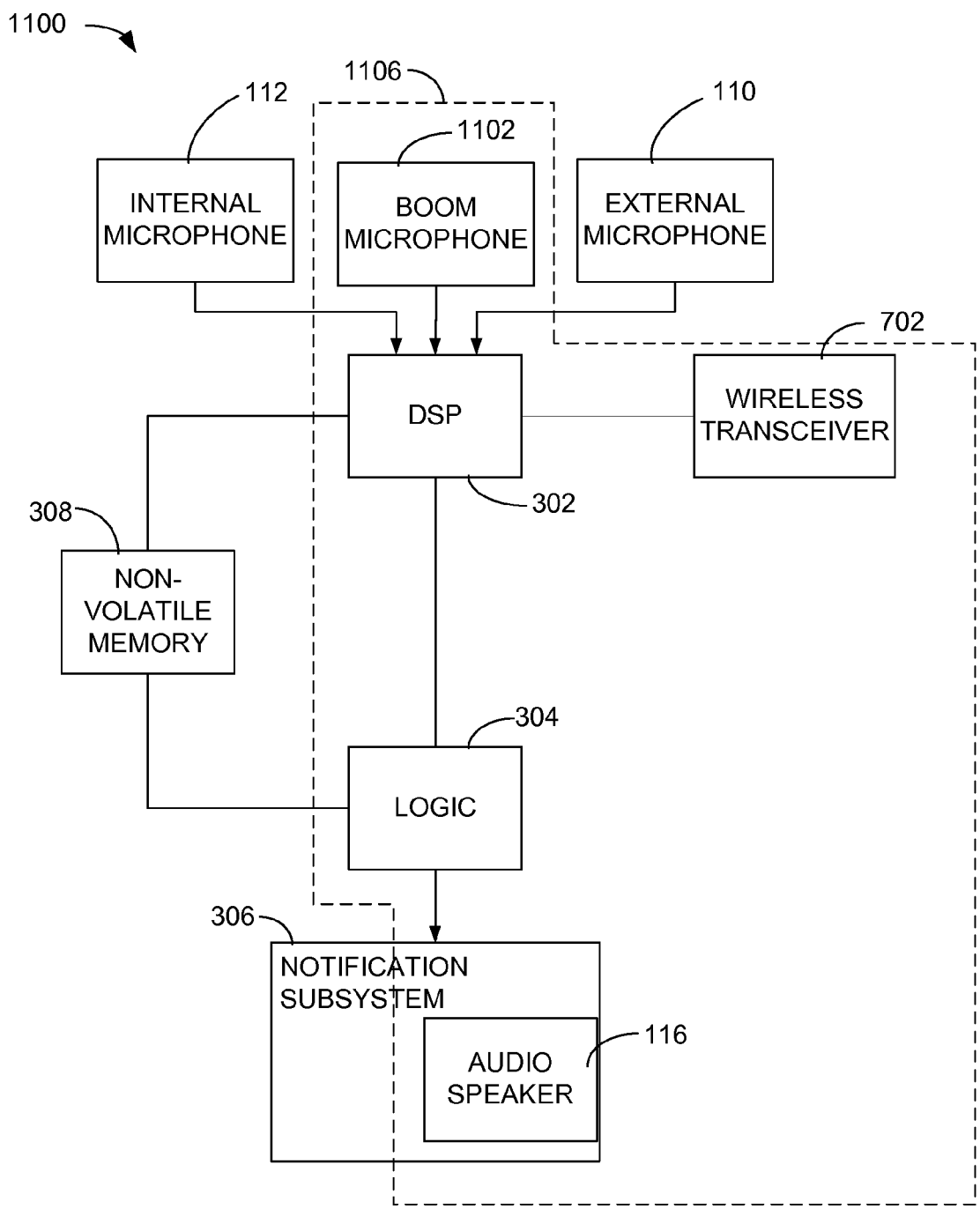
FIG. 11 is a diagrammatic view illustrating a ninth exemplary embodiment of an electronic subsystem of the headset with fit detection system of FIG. 1 usable as a wireless communication device, according to a preferred embodiment of the present invention.

FIG. 11 is a diagrammatic view illustrating a ninth exemplary embodiment of an electronic subsystem 1100 of the headset with fit detection system 100 of FIG. 1 usable as a wireless communication device 1106, according to a preferred embodiment of the present invention. Boom microphone 1102 together with wireless transceiver 702 adds wireless voice communication 1106 to the headset. The wireless voice communicator 1106 may use any available protocol. For non-limiting example, DECT, Bluetooth, or CDMA protocols may be used. Internal audio speaker 116 of the notification subsystem 306 provides the voice sound to the user. DSP 302 and logic 304 limit the sound coming from internal audio speaker 116 to ensure that the internal SPL remains within acceptable limits.

Figure 12:
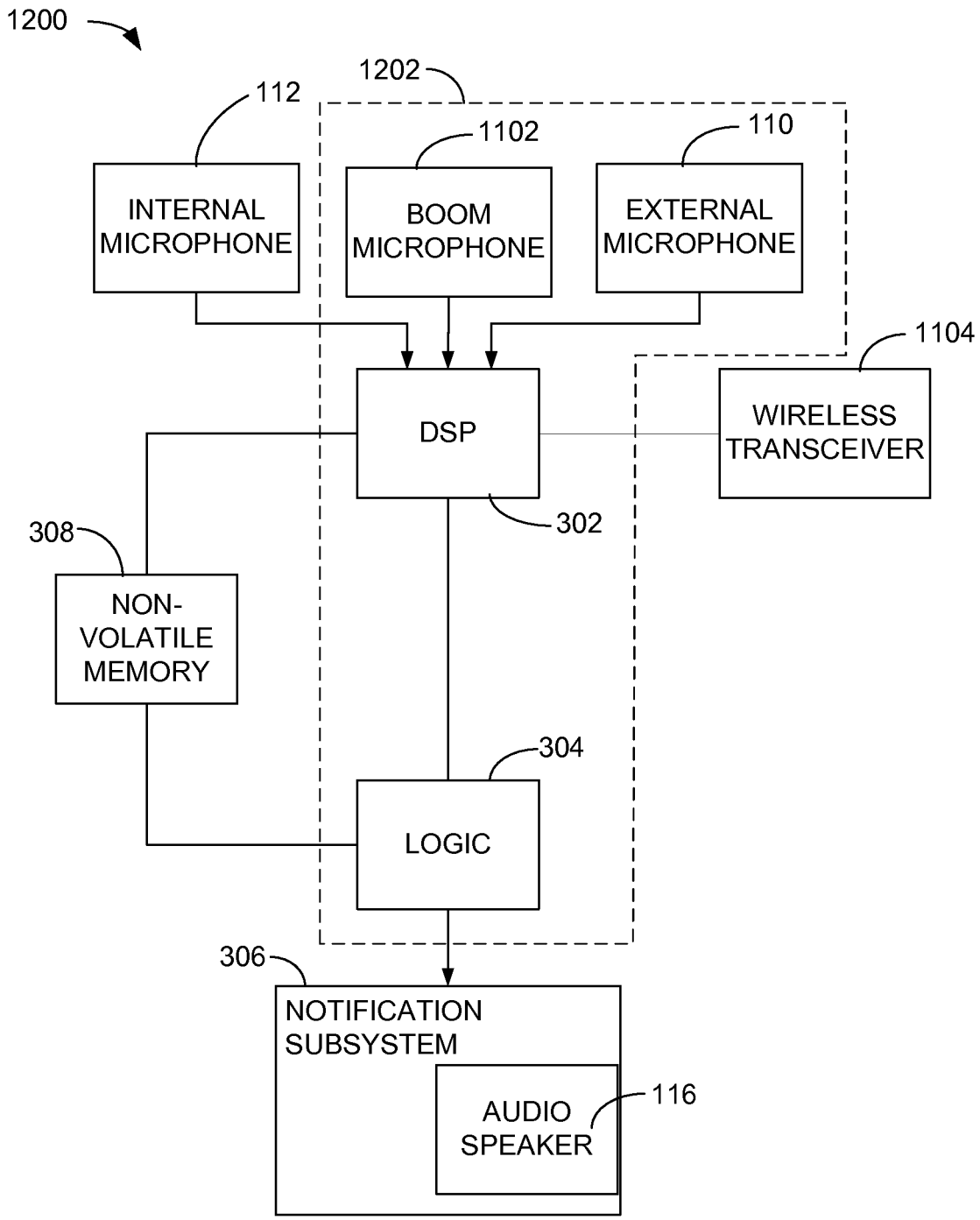
FIG. 12 is a diagrammatic view illustrating a ninth exemplary embodiment of an electronic subsystem of the headset with fit detection system of FIG. 1 usable as a wireless communication device and featuring a voice activated switch, according to a preferred embodiment of the present invention.

FIG. 12 is a diagrammatic view illustrating a tenth exemplary embodiment of an electronic subsystem 1200 of the headset with fit detection system 100 of FIG. 1 usable as a wireless voice communication device 1106 and featuring a voice activated switch 1202, according to a preferred embodiment of the present invention. Using the external microphone 110 as the far field microphone and the boom microphone 1102 as the near field microphone, the DSP 302 and logic 304 implement a voice activated switch 1202.

Those of skill in the art, enlightened by the present disclosure, will appreciate that the ANR 502 or 602, wireless voice communicator with sound limiting 1106, wireless data transmission 702, sound dosimeter 804 or 904, voice activated switch 1202, and bandpass filtering 402 and/or 404 for monitoring problematic frequencies, may all, or in any combination, be concurrently implemented in the headset with fit detection system 100. The headset with fit detection system 100, and the addition of additional disclosed features using elements of the headset with fit detection system 100, are some novel aspects of the present invention.

Although applicant has described applicant's preferred embodiments of this invention, it will be understood that the broadest scope of this invention includes such modifications as diverse shapes and sizes and materials. Such scope is limited only by the above specification and the claims below.

Further, many other advantages of applicant's invention will be apparent to those skilled in the art from the above descriptions.

We claim:

1. A headset having hearing protection for at least one of its purposes, the headset comprising:
   a. at least one ear cup having a sound-resistant edge seal;
   b. at least one first microphone mounted on the exterior of said at least one ear cup;
   c. at least one second microphone mounted on the interior of said at least one ear cup;
   d. a signal processor, coupled to said at least one first microphone and to said at least one second microphone, for computing external and internal sound pressure levels, respectively, from at least one first and at least one second signals from said at least one first microphone and said at least one second microphone, respectively; and
   e. a non-volatile memory coupled to said signal processor for storing a constant representing a fit allowance, wherein said fit allowance is a number representing the predetermined difference between said internal sound pressure level and said external sound pressure level when said headset is worn properly.

2. The headset of claim 1, further comprising a logic coupled to said signal processor and to said non-volatile memory and operable to:
   a. add said constant to said internal sound pressure level to obtain an adjusted internal sound pressure level; and
   b. compare said adjusted internal sound pressure level to said external sound pressure level to determine if said external sound pressure level is greater than or equal to said adjusted internal sound pressure level; and
   c. at least one notification system coupled to said logic and responsive to said determination to produce a notification if said determination is that said external sound pressure level is not greater than or equal to said adjusted internal sound pressure level.

3. The headset of claim 1, wherein:
   a. said at least one first microphone comprises a plurality of first microphones at least one of which has an output signal bandpass-filtered for a predetermined frequency band that is a subset of a human audio frequency band; and
   b. said at least one second microphone comprises a plurality of second microphones at least one of which has an output signal bandpass-filtered for a predetermined frequency band that is a subset of said human audio frequency band.

4. The headset of claim 2, wherein said at least one notification device comprises at least one audio speaker inside said at least one ear cup.

5. The headset of claim 4, wherein said signal processor and said logic implement active noise reduction using one of:
   a. said at least one first signal and said at least one audio speaker; and
   b. said at least one second signal as a feedback signal and said at least one audio speaker.

6. The headset of claim 4, wherein said signal processor and said logic implement active noise reduction using said at least one first signal, said at least one second signal, and said at least one audio speaker.

7. The headset of claim 4, further comprising a wireless receiver communicatively coupled to said signal processor and coupled to said audio speaker for receiving wireless audio communications in said at least one ear cup.

8. The headset of claim 2, further comprising a volatile memory coupled to said signal processor and to said logic.

9. The headset of claim 8, wherein said signal processor and said logic implement a sound dosimeter using said at least one second signal and said volatile memory.

10. The headset of claim 9, wherein said at least one notification device comprises a plurality of notification devices, at least one of which is operable to provide information related to an output of said sound dosimeter in human-readable form.

11. The headset of claim 2, wherein said at least one notification system comprises at least one of:
    a. an audio speaker mounted inside said at least one ear cup;
    b. a tactile stimulator mounted on said headset;
    c. a visual stimulator mounted on said headset; and
    d. a wireless transmitter mounted on said headset, a wireless receiver, and a display device operable to display information related to said notification in human-readable form.

12. The headset of claim 1, further comprising a boom microphone mounted on said headset and capable of being oriented near a user's mouth, an audio speaker mounted inside said at least one ear cup, a wireless transmitter mounted on said headset, and a wireless receiver mounted on said headset, together operable to provide wireless audio communication.

13. The headset of claim 12, wherein said signal processor and said logic restrict an output of said audio speaker sound power level to maintain a sound power level inside said at least one ear cup below a predetermined limit.

14. The headset of claim 12, wherein said signal processor and said logic implement a voice-activation switch using said at least one first microphone and said boom microphone.

15. A headset having hearing protection for at least one of its purposes, the headset comprising:
    a. at least one ear cup having a sound-resistant edge seal;
    b. at least one first microphone mounted on the exterior of said at least one ear cup;
    c. at least one second microphone mounted on the interior of said at least one ear cup;
    d. a signal processor, coupled to said at least one first microphone and to said at least one second microphone, for computing external and internal sound pressure levels, respectively, from at least one first and at least one second signals from said at least one first microphone and said at least one second microphone, respectively;
    e. a non-volatile memory coupled to said signal processor for storing a constant representing a fit allowance, wherein said fit allowance is a number representing the predetermined difference between said internal sound pressure level and said external sound pressure level when said headset is worn properly;
    f. a logic coupled to said signal processor and to said non-volatile memory and operable to:
       i. add said constant to said internal sound pressure level to obtain an adjusted internal sound pressure level; and
       ii. compare said adjusted internal sound pressure level to said external sound pressure level to determine if said external sound pressure level is greater than or equal to said adjusted internal sound pressure level;
    g. at least one notification system coupled to said logic and responsive to said determination to produce a notification if said determination is that said external sound pressure level is not greater than or equal to said adjusted internal sound pressure level; and
    h. a volatile memory coupled to said signal processor and to said logic.

16. The headset of claim 15, wherein
    a. said at least one first microphone comprises a plurality of first microphones at least one of which has an output signal bandpass-filtered for a predetermined frequency band that is a subset of a human audio frequency band; and
    b. said at least one second microphone comprises a plurality of second microphones at least one of which has an output signal bandpass-filtered for a predetermined frequency band that is a subset of a human audio frequency band.

17. The headset of claim 15, wherein said at least one notification system comprises at least one of:
    a. an audio speaker mounted inside said at least one ear cup;
    b. an audio speaker mounted on said headset;
    c. a tactile stimulator mounted on said headset;
    d. a visual stimulator mounted on said headset; and
    e. a wireless transmitter mounted on said headset, a wireless receiver, and a display device operable to display information related to said at least one notification in human-readable form.

18. The headset of claim 15, wherein said signal processor and said logic implement at least one of:

a. active noise reduction using said at least one first signal as a feed forward signal and said at least one audio speaker;
b. active noise reduction using said at least one first signal as a feed forward signal, at least one second signal as a feedback signal, and said at least one audio speaker;
c. active noise reduction using said at least one second signal as a feedback signal and said at least one audio speaker;
d. a voice-activation switch using said at least one first microphone and a boom microphone coupled to said headset; and
e. a sound dosimeter using said at least one second signal and said volatile memory, wherein said at least one notification system includes a subsystem operable to provide information related to an output of said sound dosimeter in at least one of machine-readable and human-readable form.

19. A headset having hearing protection for at least one of its purposes, the headset comprising:
a. at least one ear cup having a sound-resistant edge seal;
b. at least one first microphone mounted on the exterior of said at least one ear cup;
c. at least one second microphone mounted on the interior of said at least one ear cup;
d. a signal processor, coupled to said at least one first microphone and to said at least one second microphone, for computing external and internal sound pressure levels, respectively, from at least one first and at least one second signals from said at least one first microphone and said at least one second microphone, respectively;
e. a non-volatile memory coupled to said signal processor for storing a constant representing a fit allowance, wherein said fit allowance is a number representing the predetermined difference between said internal sound pressure level and said external sound pressure level when said headset is worn properly;
f. a logic coupled to said signal processor and to said non-volatile memory and operable to:
 i. add said constant to said internal sound pressure level to obtain an adjusted internal sound pressure level; and
 ii. compare said adjusted internal sound pressure level to said external sound pressure level to determine if said external sound pressure level is greater than or equal to said adjusted internal sound pressure level;
g. at least one notification system coupled to said logic and responsive to said determination to produce a notification if said determination is that said external sound pressure level is not greater than or equal to said adjusted internal sound pressure level;
h. wherein said at least one notification system comprises at least one of:
 i. an audio speaker mounted inside said at least one ear cup;
 ii. an audio speaker mounted on said headset;
 iii. a tactile stimulator mounted on said headset;
 iv. a visual stimulator mounted on said headset; and
 v. a wireless transmitter mounted on said headset, a wireless receiver, and a display device operable to display a notification in at least one of machine-readable and human-readable form;
i. a volatile memory coupled to said signal processor and to said logic.

20. The headset of claim 19, wherein:
a. said at least one first microphone comprises a plurality of first microphones at least one of which has an output signal bandpass-filtered for a predetermined frequency band that is a subset of a human audio frequency band;
b. said at least one second microphone comprises a plurality of second microphones at least one of which has an output signal bandpass-filtered for a predetermined frequency band that is a subset of a human audio frequency band; and
c. wherein said signal processor and said logic additionally implement at least one of:
 i. active noise reduction using said at least one first signal as a feed forward signal and said at least one audio speaker;
 ii. active noise reduction using said at least one first signal as a feed forward signal, at least one second signal as a feedback signal, and said at least one audio speaker;
 iii. active noise reduction using said at least one second signal as a feedback signal and said at least one audio speaker;
 iv. a voice-activation switch using said at least one first microphone and a boom microphone coupled to said headset; and
 v. a sound dosimeter using said at least one second signal and said volatile memory, wherein said at least one notification system includes a subsystem operable to provide notification of an output of said sound dosimeter in at least one of machine-readable and human-readable form.

* * * * *